United States Patent
Kopelman

(10) Patent No.: US 10,952,816 B2
(45) Date of Patent: Mar. 23, 2021

(54) VISUAL PROSTHETIC AND ORTHODONTIC TREATMENT PLANNING

(71) Applicant: Align Technology, Inc., San Jose, CA (US)

(72) Inventor: Avi Kopelman, Palo Alto, CA (US)

(73) Assignee: ALIGN TECHNOLOGY, INC., San Jose, CA (US)

(*) Notice: Subject to any disclaimer, the term of this patent is extended or adjusted under 35 U.S.C. 154(b) by 120 days.

(21) Appl. No.: 16/256,914

(22) Filed: Jan. 24, 2019

(65) Prior Publication Data
US 2019/0231478 A1    Aug. 1, 2019

Related U.S. Application Data

(60) Provisional application No. 62/622,728, filed on Jan. 26, 2018.

(51) Int. Cl.
*G06K 9/00* (2006.01)
*A61C 7/00* (2006.01)
(Continued)

(52) U.S. Cl.
CPC .............. *A61C 7/002* (2013.01); *A61B 34/00* (2016.02); *A61B 34/10* (2016.02); *A61C 1/082* (2013.01);
(Continued)

(58) Field of Classification Search
None
See application file for complete search history.

(56) References Cited

U.S. PATENT DOCUMENTS

| 2,467,432 A | 4/1949 | Kesling et al. |
| 3,407,500 A | 10/1968 | Kesling et al. |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.
(Continued)

*Primary Examiner* — Shervin K Nakhjavan
(74) *Attorney, Agent, or Firm* — Wilson Sonsini Goodrich & Rosati

(57) ABSTRACT

Systems and methods for improved visual prosthetic and orthodontic treatment planning are provided herein. In some aspects, a method for preparing a tooth of a patient is disclosed. The method may comprise building a model of a dentition of the patient including a model of the initial shape of tooth. The method may also include determining a final prepared shape of the tooth. In some aspects, the method may also include generating a treatment plan comprising a plurality of steps to modify the initial shape of the tooth to the final prepared shape of the tooth. The method may also include rendering visualizations for the plurality of steps of the treatment plan. The visualizations may depict the removal of tooth material to modify the initial shape of the tooth to the final prepared shape of the tooth.

28 Claims, 9 Drawing Sheets

(51) Int. Cl.
  *A61C 9/00* (2006.01)
  *A61C 13/00* (2006.01)
  *A61B 34/10* (2016.01)
  *A61C 1/08* (2006.01)
  *A61B 34/00* (2016.01)
  *G16H 50/50* (2018.01)

(52) U.S. Cl.
  CPC ........ *A61C 9/0053* (2013.01); *A61C 13/0004* (2013.01); *A61B 2034/102* (2016.02); *A61B 2034/105* (2016.02); *G16H 50/50* (2018.01)

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A * | 10/1996 | Mushabac .......... A61C 13/0004 433/215 |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |

(56) References Cited

U.S. PATENT DOCUMENTS

| | | | |
|---|---|---|---|
| 6,382,975 | B1 | 5/2002 | Poirier et al. |
| 6,398,548 | B1 | 6/2002 | Muhammad et al. |
| 6,402,707 | B1 | 6/2002 | Ernst et al. |
| 6,482,298 | B1 | 11/2002 | Bhatnagar et al. |
| 6,524,101 | B1 | 2/2003 | Phan et al. |
| 6,554,611 | B2 | 4/2003 | Shishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 7,433,810 | B2 * | 10/2008 | Pavloskaia ............. G16H 50/50 703/6 |
| 8,126,726 | B2 * | 2/2012 | Matov .................... A61C 7/002 705/2 |
| 8,562,338 | B2 * | 10/2013 | Kitching ................. A61C 7/00 433/24 |
| 8,923,581 | B2 * | 12/2014 | Souza .................... G06T 7/162 382/128 |
| 9,592,103 | B2 * | 3/2017 | Taub ...................... G06N 5/046 |
| 9,597,165 | B2 * | 3/2017 | Kopelman ............. G05B 17/02 |
| 1,012,370 | A1 | 11/2018 | Elbaz et al. |
| 10,624,717 | B2 * | 4/2020 | Wen ........................ A61C 9/004 |
| 2002/0006597 | A1 | 1/2002 | Andreiko et al. |
| 2002/0150859 | A1 | 10/2002 | Imgrund et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer et al. |
| 2004/0128010 | A1 | 7/2004 | Pavlovskaia et al. |
| 2005/0055118 | A1 | 3/2005 | Nikolskiy et al. |
| 2006/0064329 | A1 * | 3/2006 | Abolfathi ............... B33Y 80/00 705/3 |
| 2010/0009308 | A1 * | 1/2010 | Wen ........................ A61C 7/08 433/24 |
| 2010/0145898 | A1 * | 6/2010 | Malfliet ................. G06T 7/0012 706/47 |
| 2013/0110469 | A1 * | 5/2013 | Kopelman ............. G06T 19/20 703/1 |
| 2014/0322664 | A1 | 10/2014 | Van et al. |
| 2015/0305830 | A1 * | 10/2015 | Howard .................... A61C 7/08 433/6 |
| 2016/0128624 | A1 * | 5/2016 | Matt ..................... A61B 5/1128 600/301 |
| 2017/0372032 | A1 | 12/2017 | Kuo et al. |
| 2019/0038367 | A1 * | 2/2019 | Ciriello .................. A61B 34/00 |
| 2019/0046276 | A1 * | 2/2019 | Inglese ................ A61C 9/0046 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL< http://astronomy. swin.edu.au/—pbourke/prolection/coords>.

Boyd et al., "Three Dimensional Diagnosis and Orthodontic Treatment of Complex Malocclusions With the Invisalign Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

(56) References Cited

OTHER PUBLICATIONS

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, "Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).

Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-ALLDENT Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-328 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.

(56) References Cited

OTHER PUBLICATIONS

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

PCT/US2019/015032 International Search Report and Written Opinion dated Jul. 2, 2019. 17 pages.

Pinkham, "Foolish Concept Propels Technology," Dentist, 3 pages total, Jan./Feb. 1989.

Pinkham, "Inventors CAD/CAM May Transform Dentistry," Dentist, 3 pages total, Sep. 1990.

Ponitz, "Invisible Retainers," Am. J. Orthod., 59(3):266-272 (Mar. 1971).

Procera Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993.

Raintree Essix & ARS Materials, Inc., Raintree Essix, Technical Magazine Table of contents and Essix Appliances,< http:// www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art'?", J. Amer. Dent. Assoc., 122:43-48 1991.

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording the Dental Cast in Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Sur9., 114:438-442 (Apr. 1988).

Schroeder et al., Eds. The Visual Toolkit, Prentice Hall PTR, New Jersey (1998) Chapters 6, 8 & 9, (pp. 153-210,309-354, and 355-428, respectively.

Shilliday, (1971). Minimizing finishing problems with the mini-positioner, Am. J. Orthod. 59:596-599.

Siemens, "CEREC—Computer-Reconstruction," High Tech in der Zahnmedizin, 14 pages total (2004).

Sinclair, "The Readers' Corner," J. Clin. Orthod., 26(6):369-372 (Jun. 1992).

Sirona Dental Systems GmbH, CEREC 3D, Manuel utiiisateur, Version 2.0X (in French), 2003,114 pages total.

Stoll et al., "Computer-aided Technologies in Dentistry," (article summary in English, article in German), Dtsch Zahna'rztl Z 45, pp. 314-322 (1990).

Sturman, "Interactive Keyframe Animation of 3-D Articulated Models," Proceedings Graphics Interface '84, May-Jun. 1984, pp. 35-40.

The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).

The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).

(56) References Cited

OTHER PUBLICATIONS

The Choice Is Clear: Red, White & Blue . . . The Simple, Affordable, No-Braces Treatment, Allesee Orthodontic Appliances—Pro Lab product information, 6 pages (2003).

The Red, White & Blue Way to Improve Your Smile! Allesee Orthodontic Appliances—Pro Lab product information for patients, 2 pages 1992.

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (1996).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden, "A New Method to Determine Tooth Positions and Dental Arch Dimensions," J. Dent. Res., 51(4):1104 (Jul.-Aug. 1972).

Van Der Linden et al., "Three-Dimensional Analysis of Dental Casts by Means of the Optocom," J. Dent. Res., p. 1100 (Jul.-Aug. 1972).

Van Der Zel, "Ceramic-Fused-to-Metal Restorations with a New CAD/CAM System," Quintessence Int., 24(11):769-778 (1993.

Varady et al., "Reverse Engineering of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).

Warunek et al.: Physical and Mechanical Properties of Elastomers in Orthodonic Positioners, Am J. Orthod. Dentofac. Orthop, vol. 95, No. 5, (May 1989) pp. 388-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances—Pro Lab product information for patients, 2 pages (2002).

* cited by examiner

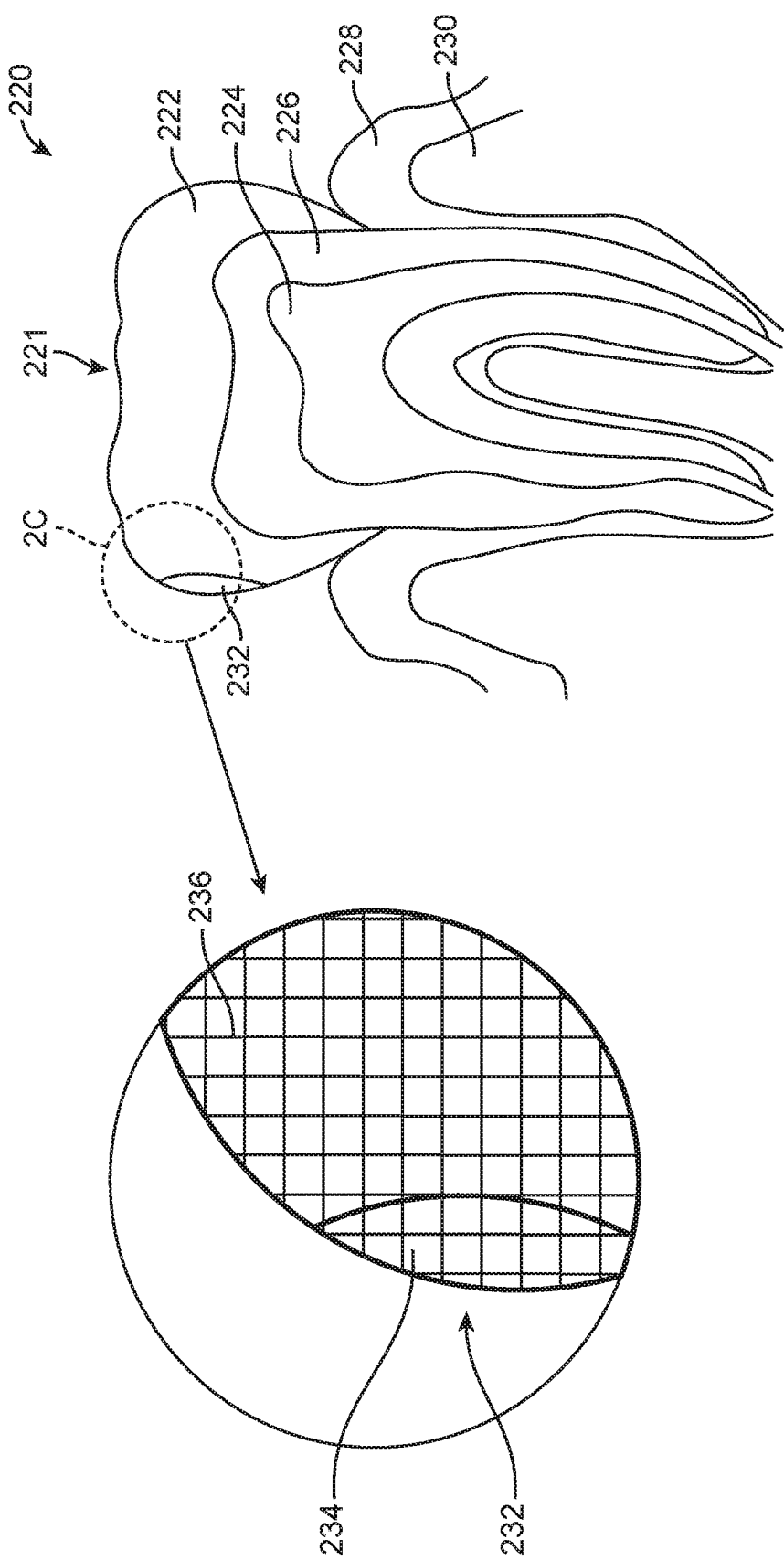

VISUAL PROSTHETIC AND ORTHODONTIC TREATMENT PLANNING

CROSS-REFERENCE

This application claims the benefit of U.S. Provisional Application No. 62/622,728, filed Jan. 26, 2018, which application is incorporated herein by reference.

BACKGROUND

Prior prosthetic and orthodontic procedures typically involve preparing teeth for receiving prosthetics and for orthodontic movement. Preparation for these treatments may include material removal to shape the teeth to receive a prosthetic or material removal to provide space for orthodontic movement such as interproximal reduction. To achieve these objectives, a dental practitioner may use various tools to remove material when shaping the teeth. The dental practitioner may make an educated guess as to the appropriate tools to use, and when and how to use them.

Sometimes, these prior prosthetic and orthodontic methods and systems can result in less than ideal preparation and treatment, in at least some respects. In light of the above, improved prosthetic and orthodontic treatment planning, preparation, and treatment are needed. Ideally such prosthetic and orthodontic treatment planning, preparation, and treatment would provide more reliable and easier to follow treatment steps, more accurately prepared teeth, and greater dental practitioner confidence.

SUMMARY

Improved systems, methods, and devices for repositioning a patient's teeth are provided herein. In some aspects a method for preparing a tooth of a patient is disclosed. The method may include building a model of a dentition of the patient including a model of the initial shape of tooth. The method may also include determining a final prepared shape of the tooth. In some aspects the method may include generating a treatment plan comprising a plurality of steps to modify the initial shape of the tooth to the final prepared shape of the tooth. The method may also include rendering visualizations for the plurality of steps of the treatment plan, the visualizations depicting the removal of tooth material to modify the initial shape of the tooth to the final prepared shape of the tooth.

In some embodiments, the method may include building a three-dimensional surface model of the patient's dentition from a three-dimensional surface scan of the patient's dentition, building a volumetric model from an infrared scan of an internal structure of the patient's dentition, and building a composite model from the three-dimensional surface model and the volumetric model.

In some aspects the three-dimensional, composite or volumetric model comprises a plurality of voxels. The voxels may include a location within the composite or volumetric model, a dental structure type of the internal structure, and a density. A voxel may further comprise a defect type.

In some embodiments, the dental structure type of the internal structure, the density, and the defect type may be determined based on the infrared scan of the internal structure of the patient's dentition or an x-ray image of the internal structure of the patient's dentition.

In some embodiments, a method may include determining the material removed for each step of the treatment plan and may also include selecting a tool from a plurality of tools for removing tooth material for each of the plurality of steps and selecting a tool head from a plurality of tool heads for removing tooth material for each of the plurality of steps.

In some aspects, the method may include determining a movement path for each selected tool for removing material for the plurality of steps in the treatment plan. The movement path may include an indication of a direction of translation and an orientation of the tool head. The visualization may be a three-dimensional visualization. The visualization may be a three-dimensional, video simulation of the material removal for the plurality of steps of the treatment plan.

The method may include reimaging a patient's dentition after removing a portion of material according to a step of the treatment plan to build an updated model of a dentition including an updated model of the patient's tooth, comparing the updated model of a dentition with a model of the dentition for the step of the treatment plan, and highlighting remaining material that should be removed according to the step of the treatment plan. In some embodiments, the method may include determining an updated final prepared shape of the tooth, generating an updated treatment plan comprising a second plurality of steps to modify the updated model shape of the tooth to the updated final prepared shape of the tooth, and rendering second visualizations for the second plurality of steps of the updated treatment plan, the second visualizations depicting the removal of tooth material to modify the updated model shape of the tooth to the updated final prepared shape of the tooth. The final prepared shape of the tooth may be the same as the updated final prepared shape of the tooth.

In some aspects, the method may include receiving constraints on the final prepared shape of the tooth, and generating a plurality suggested final prepared shapes of the tooth based on the constraints. The method may also include receiving a selection of the final prepared shape from the plurality of suggested final prepared shapes, and determining the final prepared shape of the tooth is based on the received selection of the final prepared shape.

A system for aiding in preparing a tooth of a patient is also disclosed. The system may include one or more processors and memory, wherein the memory comprises instructions executable by the one or more processors to cause the system to build a model of a dentition of the patient including a model of the initial shape of tooth, generate a treatment plan comprising a plurality of steps to modify the initial shape of the tooth to a final prepared shape of the tooth, and render visualizations for the plurality of steps of the treatment plan, the visualizations depicting the removal of tooth material to modify the initial shape of the tooth to the final prepared shape of the tooth.

In some embodiments, the memory further comprising instructions executable by the one or more processors to cause the system to build a three-dimensional surface model of the patient's dentition from a three-dimensional surface scan of the patient's dentition and combine the three-dimensional surface model of the patient's dentition with an imagery of the internal structure of the patient's dentition to form a three-dimensional, composite model of the patient's dentition.

The three-dimensional, volumetric model may be a plurality of voxels. The voxels may comprise a location within the volumetric model, a dental structure type of the internal structure, and a density. The voxel further may comprise a defect type. The dental structure type of the internal structure, the density, and the defect type may be determined based on an infrared scan of the internal structure of the patient's dentition or an x-ray image of the internal structure of the patient's dentition or based on other imaging, such as ultra sound, MM, OCT, and others.

In some embodiments, the memory further comprising instructions executable by the one or more processors to cause the system to determine the material removed for each step of the treatment plan. The system may also be configured to select a tool from a plurality of tools for removing tooth material for each of the plurality of steps, and select a tool head from a plurality of tool heads for removing tooth material for each of the plurality of steps.

In some aspects, the memory further comprising instructions executable by the one or more processors to cause the system to determine a movement path for each selected tool for removing material for the plurality of steps in the treatment plan. The movement path may include an indication of a direction of translation and an orientation of the tool head. The visualization may be a three-dimensional visualization. The visualization may be a three-dimensional, video simulation of the material removal for the plurality of steps of the treatment plan.

The system may be configured to receive an updated image of a patient's dentition after removing a portion of material according to a step of the treatment plan to build an updated model of a dentition including an updated model of the patient's tooth, compare the updated model of a dentition with a model of the dentition for the step of the treatment plan, and highlight remaining material that should be removed according to the step of the treatment plan.

In some embodiments, the system may be configured to determine an updated final prepared shape of the tooth, generate an updated treatment plan comprising a second plurality of steps to modify the updated model shape of the tooth to the updated final prepared shape of the tooth, and render second visualizations for the second plurality of steps of the updated treatment plan, the second visualizations depicting the removal of tooth material to modify the updated model shape of the tooth to the updated final prepared shape of the tooth. The final prepared shape of the tooth may be the same as the updated final prepared shape of the tooth.

In some aspects, the system may be configured to receive constraints on the final prepared shape of the tooth; and generate a plurality suggested final prepared shapes of the tooth based on the constraints. The memory further comprises instructions executable by the one or more processors to cause the system to receive a selection of the final prepared shape from the plurality of suggested final prepared shapes, and wherein determining the final prepared shape of the tooth is based on the received selection of the final prepared shape.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B illustrates cross-section of a three dimensional image, in accordance with embodiments;

FIG. 2C illustrates a detail of a portion of the three dimensional image of FIG. 2B, in accordance with embodiments;

DETAILED DESCRIPTION

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail herein. Various other modifications, changes, and variations which will be apparent to those skilled in the art may be made in the arrangement, operation, and details of the methods, systems, and apparatus of the present disclosure provided herein without departing from the spirit and scope of the invention as described herein.

As used herein the term "and/or" is used as a functional word to indicate that two words or expressions are to be taken together or individually. For example, A and/or B encompasses A alone, B alone, and A and B together.

As used herein a "plurality of teeth" encompasses two or more teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The present disclosure provides systems and related methods for planning tooth preparation procedures and for carrying out tooth preparation procedures.

Figure 1:
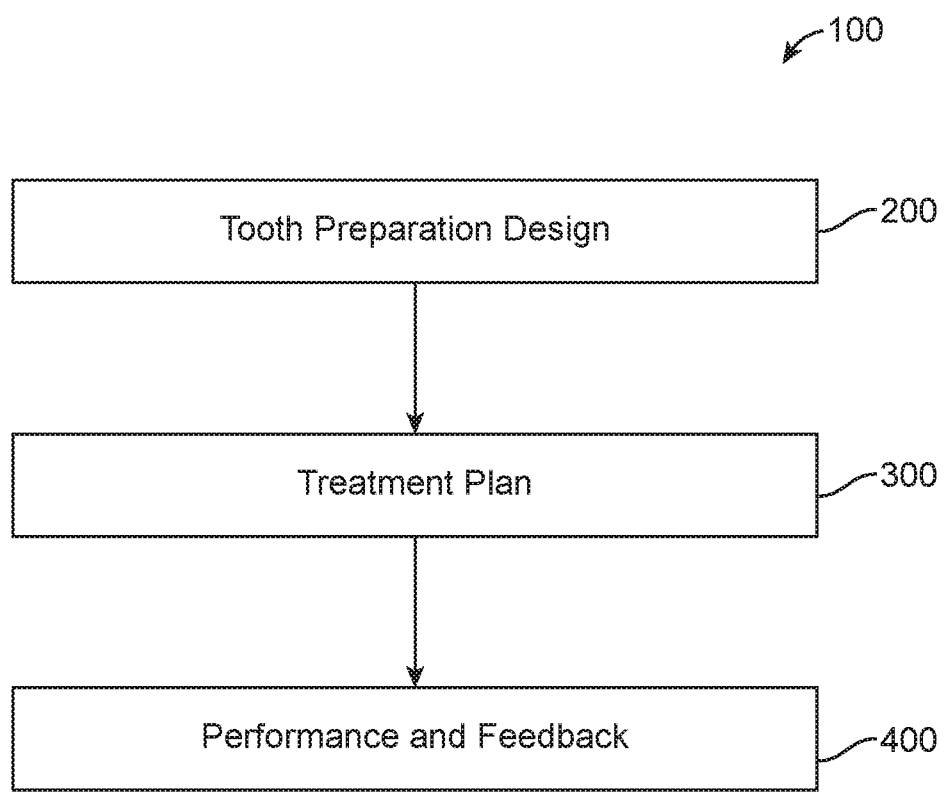
FIG. 1 illustrates a method for planning the preparation of teeth and preparing teeth, in accordance with embodiments.

Turning now to the drawings, in which like numbers designate like elements in the various figures, FIG. 1 illustrates method 100 for preparing and treating teeth, in accordance with embodiments disclose herein. The method 100 for preparing and treating teeth includes tooth preparation and design at block 200, development of a treatment plan at block 300, and performance and feedback at block 400. At block 200 a dental practitioner may make multiple records of the patient. The records may include various imaging records. For example, the dental practitioner may scan the patient's dentition with an intra-oral scanner to build a three-dimensional surface model of the patient's dentition. The dental practitioner may also compile other two-dimensional and three-dimensional images and models, such as, ultra sound, MM, OCT, x-ray images and volumetric data from CBCT scans or transillumination scans, or volumetric models generated by the methods and systems described in U.S. Ser. No. 15/662,234, incorporated herein by reference in its entirety, among others. The practitioner may also select the teeth to be prepared and provide additional information, such as the type of prosthetic to be placed on the teeth. Also at block 200, dental practitioner may identify tooth material that should be removed during patient treatment, such as dental caries. The dental practitioner may also indicate other treatment parameters such as the type, manufacture, and model of prosthetic to be used, and a preference for using particular types of procedures and tools.

At block 300 one or more treatment plans are prepared. Preparation of the treatment plans may include preparing multiple treatment suggestions showing the final preparation of the patient's teeth along with models of intermediate steps showing how the teeth are shaped from their initial shape to their final prepared shape. The dental professional may select a treatment plan from the multiple treatment suggestions.

After receiving a selection for a treatment plan, the material to be removed from the teeth is determined, and the tools for each step in the plan are selected. Finally, images including both static, two-dimensional images, manipulatable three-dimensional surface or volumetric models, and both static and manipulatable videos for each step and the treatment plan may be generated and displayed to the dental professional in order to aid the dental professional in carrying out treatment on the patient.

At block 400 the treatment as performed and feedback on the treatment is provided. In this process a dental professional begins removing material from the patient's teeth as indicated by the treatment plan. At any time during treatment, the dental professional may request feedback as to the progress being made. To request and receive feedback, the dental professional re-images the patient's dentition. The current physical state of the patient's dentition, as indicated by the re-imaging data, may be evaluated with reference to the treatment plan. The progress with respect to the treatment plan, and any deviations from the treatment plan, may be indicated to the dental professional. In some embodiments, the treatment plan may be revised according to the updated state of the patient's dentition and the dental professional may proceed with treatment according to the revised treatment plan. The process 100 is described in greater detail below.

One or more of the steps of the method 100 may be performed with circuitry as described herein, for example one or more of a processor or logic circuitry of a computer or a computerized system. The circuitry may be programmed to provide one or more of the steps of the method 100, and the program may comprise program instructions stored on a computer readable memory or programmed steps of the logic circuitry, for example.

Figure 2A:
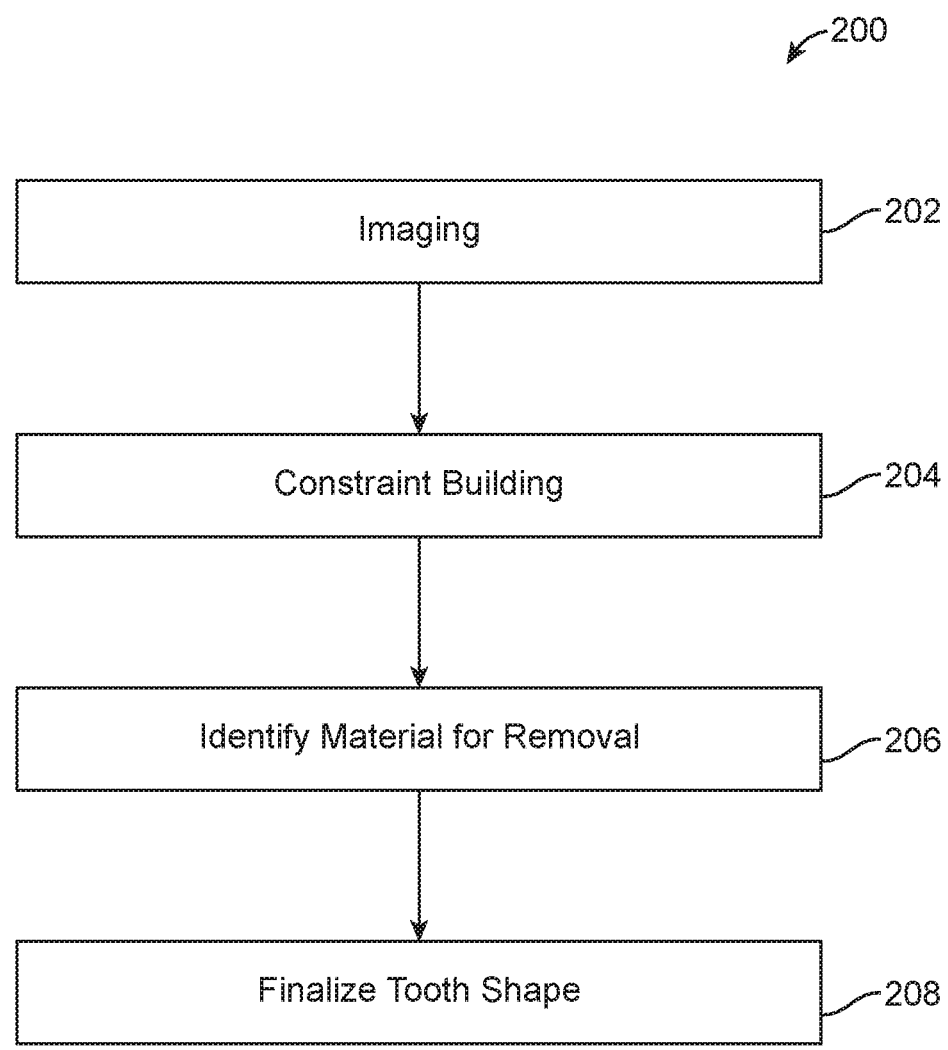
FIG. 2A illustrates a method of tooth preparation design, in accordance with embodiments.

FIG. 2A illustrates a method of tooth preparation design 200, in accordance with embodiments described herein. At block 202, the method 200 includes imaging the patient's dentition, including the patient's teeth. At block 204, the method 200 includes receiving and building of the constraints for the treatment plan. At block 206, the method 200 identifies material to be removed from the tooth in order to prepare the tooth for, for example, receiving a prosthetic. At block 208 the method 200 finalizes the shape of the tooth. Although a single tooth is referenced above, and elsewhere herein, the treatment plan and the accompanying treatment may include the preparation and treatment of multiple teeth. For example, multiple teeth may be prepared to receive a bridge or multiple prosthetics or, for example, teeth adjacent to such teeth may be prepared in order to facilitate insertion of the prosthetic. In some embodiments, teeth are prepared to accommodate orthodontic treatment. In such an embodiment, interproximal reduction may be used to provide space in the arch for tooth movement and rotation. The interproximal reduction material removal and orthodontic movement may be considered in the method of tooth preparation design 200.

A block 202, multiple different imaging and model building processes may be performed. For example a volumetric three-dimensional model of the patient's dentition may be built as described in U.S. Ser. No. 15/662,234, previously incorporated by reference. Two-dimensional images such as color surface images and x-ray images may be used in building the model. Color surface images may be used for color matching a prosthetic with the patient's natural teeth of for distinguishing between teeth and gingiva. Surface penetrating scans may be used to image the internal structure of the teeth. For example, X-ray images may be used to identify various internal structures of the teeth, such as the enamel and the dentin. X-ray images may also be used to identify dental caries and other defects within the teeth. Ultrasound imaging may be used to identify subsurface, internal features of the teeth. Other technologies such as infrared or near-infrared transillumination, small angle penetration imaging, or reflectance scanning may also be used to gather subsurface images of the internal features of the teeth and to aid in identifying the various internal structures within a patient's teeth.

Three-dimensional imaging or volumetric data such as from a CBCT scan or a three-dimensional surface scan of the teeth may be combined with the two-dimensional imaging data discussed above in order to build a volumetric three-dimensional, or composite, model of the patient's teeth.

FIGS. 2B and 2C depict a two-dimensional cross-section 220 of a three-dimensional volumetric model of a patient's tooth 221. As shown in FIG. 2B, an integrated volumetric model of the teeth may be formed from the combination of two-dimensional imaging data, such as X-rays and surface penetrating infrared imaging, with three-dimensional images allows for the presentation in display of both interior and exterior structures of the tooth. The innermost structures, for example the pulp 224 may be determined based on x-ray imaging. The location and volume of other interior structures of the tooth 221 may be determined based on a combination of x-ray imaging and surface penetrating infrared imaging. Such interior structures depict the extent and location of the enamel 222 and the dentin 226. In addition to modeling the interior structures of the teeth, two-dimensional and three-dimensional imaging may be used to model other structures of the patient's mouth such as the gingiva to 228 and the bone 230.

Surface penetrating infrared imaging and x-ray imaging produce two-dimensional images of the interior structure of the tooth, however, at block 202 the method 200 may combine the two-dimensional images of the interior of the tooth with generic or other, non-patient specific, models of the interior structure of a teeth to generate a three-dimensional volumetric model of the patient's tooth.

FIG. 2C shows a detailed portion of the enamel 222 of the tooth 221, including a carie 232. As discussed above, FIGS. 2B and 2C depict a portion of a volumetric model 220 of the tooth 221. A volume metric model, such as volumetric model 220, is comprised of many voxels, such as voxels 234, 236. Each voxel 234, 236 represents a discrete volume of the tooth 221. Each voxel 234, 236 may be assigned qualities such as density, dental structure type, and other properties such as whether or not a portion of the voxel includes a structural defect, such as a portion of a carie. As shown in FIG. 2C, voxel 236 is a portion of the enamel 222 of the tooth 221. Accordingly, voxel 236 may be assigned properties such as a dental structure type of enamel and a density determined based on surface penetrating infrared imaging and x-rays at the location of the voxel 236.

Voxel 234 represents a volume of the tooth 221 that is part of the enamel 222 and includes a portion of a structural defect, such as the carie 234. Accordingly, voxel 234 may be assigned properties such as a dental structure type of enamel, a defect type of carie, and a density determined based on a surface penetrating infrared image and x-ray image at the location of voxel 234. Defects may include structural defects, such as a carie, fracture, chip, lesions, or other structure defects, or non-structural defects, such as nerve decay or death, dental fillings and others.

At block 204, the method 200 includes receiving and building constraints for treatment and preparation of the tooth. The constraints may be received from the dental professional, such as their preferred tools to use, their preferred dental structures and shapes for prepared teeth, whether teeth adjacent to the prepared to may be modified to aid in treatment, and other doctor preferences.

Other constraints may be dictated by the type of prosthetic being used, its wall thickness and margin shape. For example, manufacturers of particular prosthetics may recommend certain shapes for the prepared tooth, certain minimum thicknesses, and tolerances or spacing with respect to adjacent teeth, the level of retention of the prosthetic, the margin shape, the marginal seal between the tooth in the prosthetic, and other constraints. These constraints and others may be used in determining in identifying material for removal and the final prepared shape of the tooth. In some embodiments, multiple suggested preparations are determined based on the constraints. These multiple suggested preparations may be displayed to the dental professional and a selected preparation may be you received from the dental professional.

In some embodiments, the multiple suggested preparations may be determined based on different priorities for each of the constraints. For example, in some embodiments, some constraints are mutually exclusive, for example, the dental professional may have a preference for a sub gingiva margin line and had also selected a particular prosthetic, however the prosthetic manufacture of the selected prosthetic recommends a super gingival margin preparation. Accordingly, one suggested preparation may include a sub gingival margin line and an alternative prosthetic, while a second suggested preparation may include a super gingival margin line with the selected prosthetic. Similarly, optimization of one constraint may lead to less than optimal preparation with respect to a second constraint. In such embodiments multiple suggested preparations may also be suggested. The suggested preparations may include a first suggested preparation that optimizes for the first constraint, a second suggested preparation that optimizes for the second constraint, and a third suggested preparation that balances the two constraints.

Next, at block 206, method 200 proceeds to identify the material for removal for each of the suggested preparation designs. Some of the material identified for removal may include caries within the teeth. For example, a dental professional may identify voxels that comprise a portion of a carie or other defect within the tooth from the volumetric model discussed above and shown and described, for example, with respect to FIGS. 2B and 2C. In such an embodiment, at block 206, the method marks each voxel that comprises at least a portion of the caries for removal. In other embodiments, other portions of the tooth may be identified for removal based on other constraints mentioned above, such as, the marginal seal recommended by the manufacturer of the prosthetic, the level of retention desired by the dental professional, and the material strength of the prosthetic.

Identifying the material for removal may also take into consideration the location and shape of nearby teeth. For example, proper installation of a prosthetic may dictate a particular insertion path for the prosthetic. In some embodiments the insertion path may interfere with adjacent teeth or a standard abutment shape. Accordingly, material may be removed from adjacent teeth or the tooth receiving the prosthetic in order to provide a clear and unobstructed insertion path for the prosthetic.

In some embodiments, material removal may include modeling of the interproximal and occlusion contacts to ensure that when the prosthetic is placed on the prepared tooth, the prosthetic interact properly with adjacent teeth and teeth of the opposing jaw during natural occlusion.

In some embodiments, material removal may include interproximal reduction of one or more teeth. For example, if an arch of the patient is crowded, then treatment may include determining the amount and location an interproximal reduction of the one or more teeth of the arch. In determining the amount of interproximal reduction, the method may evaluate the thickness of the enamel depicted in the biometric three-dimensional and volumetric models or other two-dimensional and three-dimensional imagery to select candidates for interproximal reduction such that the remaining enamel in each tooth of the arch is clinically acceptable.

Figure 2D:
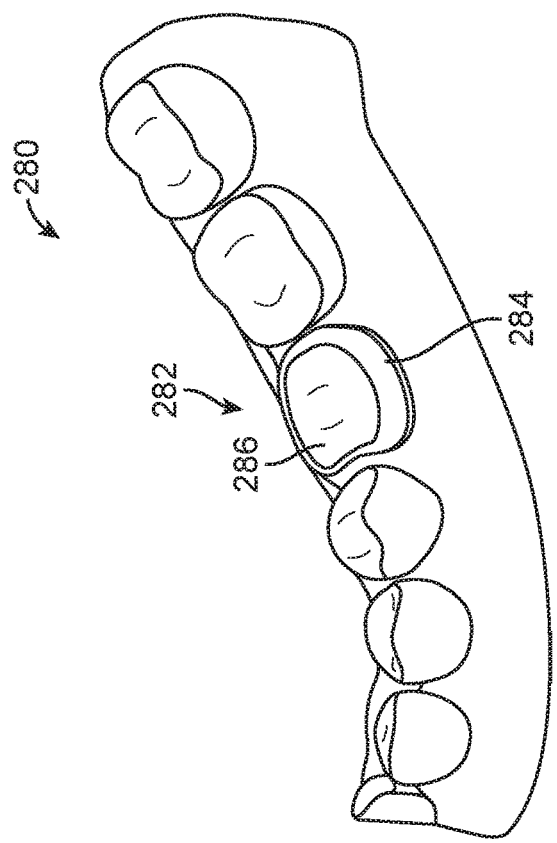
FIG. 2D illustrates a model of a dentition before preparation design and a model of dentition after preparation design, in accordance with embodiments.
Figure 2D:
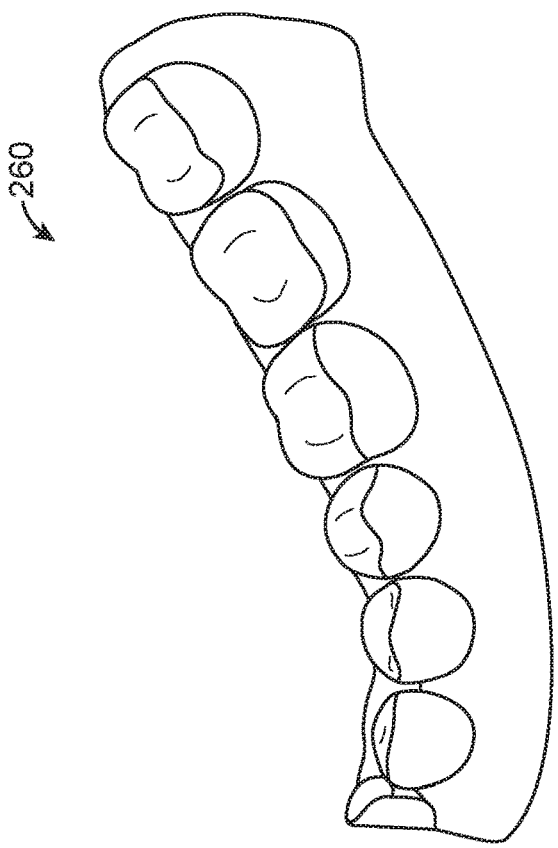

Next, at block 208, one or more suggested preparation designs are presented to the dental professional and a selected finalized shape is received. As shown in FIG. 2D, a model of the current state of the dentition 260 may be displayed along with a model 280 of the dentition with the prepared tooth 282. The model 280 shows the prepared tooth 282 including both the location and shape the margin line 284 and the prepared abutment shape 286 of the tooth 282. Some embodiments, in addition to showing the suggested preparation 280, the intermediate steps that lead to the suggested preparation 280 are also displayed for review by the dental professional into aid in determining the selected final preparation design from the one or more suggested final preparation designs. After the final preparation design is selected, the tooth shape is finalized and the process 100 proceeds to block 300.

One or more of the steps of the method 200 may be performed with circuitry as described herein, for example one or more of a processor or logic circuitry of a computer or a computerized system. The circuitry may be programmed to provide one or more of the steps of the method 200, and the program may comprise program instructions stored on a computer readable memory or programmed steps of the logic circuitry, for example.

Moving to FIG. 3, a method of treatment planning 300 is depicted in accordance with embodiments described herein. Preparation of the treatment plans may include preparing multiple treatment suggestions showing the final preparation of the patient's teeth and models of intermediate steps showing how the teeth are shaped from their initial shape to their final prepared shape for each treatment suggestion. The treatment suggestions may also depict the material removal processes using different tools or different material removal steps. The dental professional may select a treatment plan from the multiple treatment suggestions.

After selection of a treatment plan, images including both static two-dimensional images, three-dimensional models, and videos for each step of the treatment plan may be generated and displayed to the dental professional in order to aid the dental professional in carrying out treatment on the patient.

The method of treatment planning 300 may include Block 302, where the intermediate material removal steps are determined for each of the individual material removal steps. At block 304 the material to be removed for each step is identified for example by highlighting or showing in a contrasting color, as depicted in FIG. 3B.

Figure 3A:
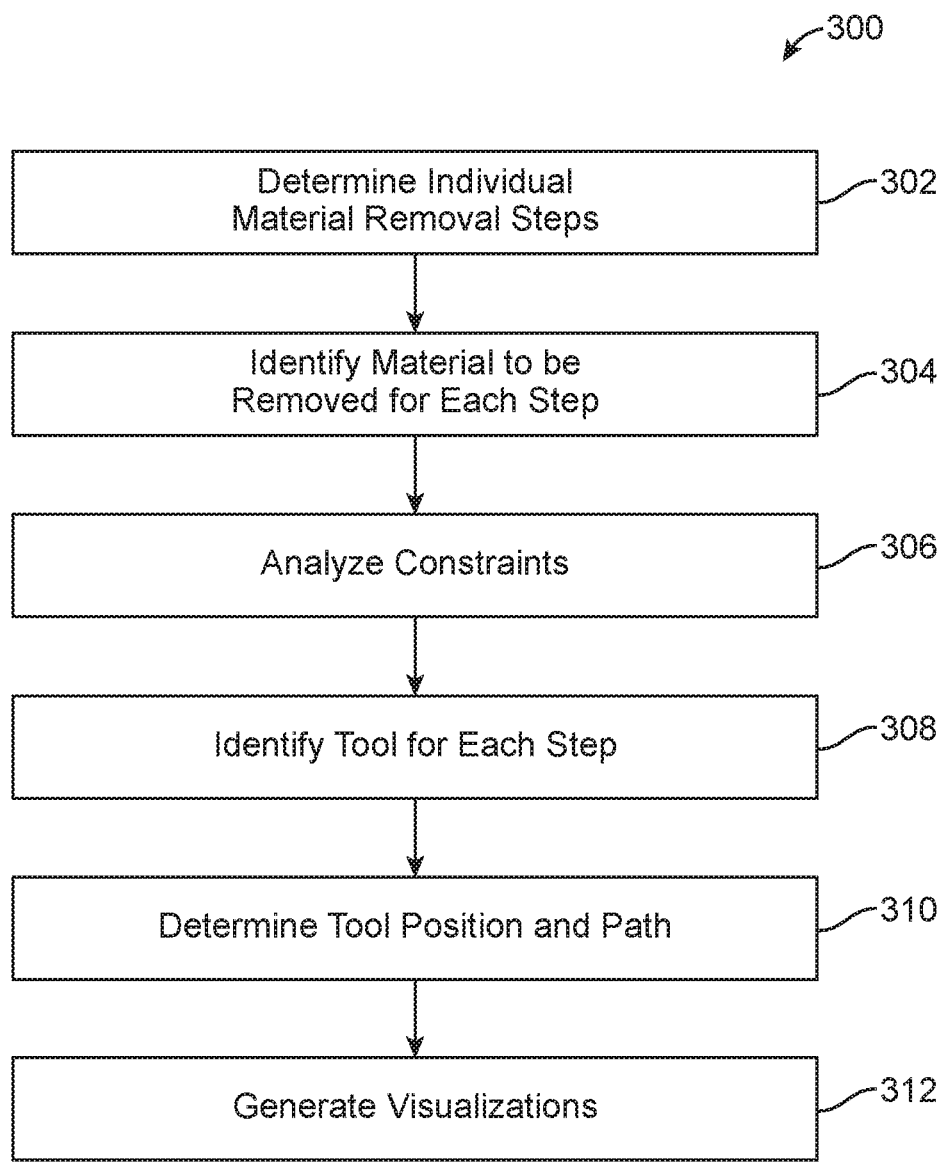
FIG. 3A illustrates a method of treatment planning, in accordance with embodiments.
Figure 3B:
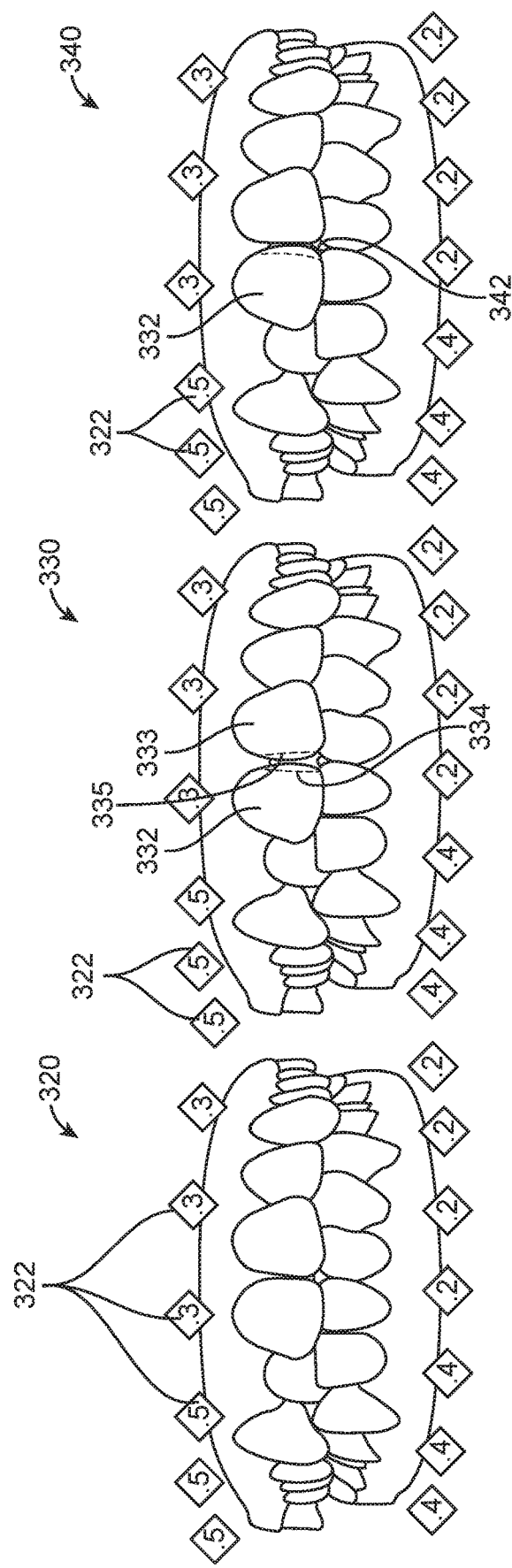
FIG. 3B illustrates the indication of material to be removed from teeth, in accordance with embodiments.

FIG. 3B depicts three models 320, 330, 340 of the teeth of a patient during a stage of treatment. Each of the models 320, 330, 340 indicate the same total amount of interproximal reductions 322 between each of the teeth depicted in the respective models. However each model displays different options for treatment with interproximal reduction. A model, such as model 320, may be shown to an experienced dental practitioner who does not desire to have each of the individual interproximal reductions highlighted, instead only using the amount of interproximal reduction indicated in the model.

Models 330, 340 may be shown to dental practitioners who desire guidance with respect to interproximal reduction or when multiple clinically acceptable types of interproximal reduction are available. The model 330, for example, shows an option for interproximal reduction where both upper central incisors 332, 333 have equal amounts of the indicated 0.3 mm of interproximal reduction 334, 335 applied to each tooth. The contrasting or highlighting of the interproximal reductions 334, 335 provides a visual guide to the dental professional when carrying out interproximal reduction on the patient and show both the location and extent of the interproximal reduction on the model. Model 340 shows an alternative interproximal reduction where material is removed from only the right upper central incisor 332. As shown in model 340, the entirety of the 0.3 mm of interproximal reduction is removed from the right central incisor 332. The models 320, 330, 340 may be presented to the dental practitioner and a selection of a desired model may be received. In some embodiments, a preferred model may be presented that is based in part on volumetric data of the teeth where interproximal reduction is desired. For example, if the volumetric data or other surface penetrating image data (e.g., x-ray, CBCT, etc.) suggests that both teeth have equal amounts of enamel, then the interproximal reduction may be equally distributed between the teeth. In other examples, if the volumetric data or other surface penetrating image data suggest that one tooth has more enamel compared to the adjacent tooth, then the interproximal reduction may be distributed more toward the tooth with more enamel (e.g., weighted or proportioned depending on the differences in enamel thickness between the teeth).

Moving to block 306, constraints for tool selection are received or otherwise determined. Constraints may include physical constraints such as the size or dimensions of the patient's mouth and entry into the oral cavity. For example, children have a relatively small opening that may dictate that only certain smaller tools may be used during the procedure. In some embodiments, a patient may have physical restrictions on the degree to which they can open their mouth that may also dictate that smaller tools are used. In addition, other constraints may include a doctor's preference for a certain type of tool and burr heads. In another example, in patients with large oral cavities, tools having additional reach or length or a particular minimum reach or length may be used as a constraint, while shorter tools are not considered.

After the constraints are received and analyzed at block 306, the method 300 continues to block 308 where the tools are determined for each step of the treatment. The tools, including both hand tools and tool heads are determined based on the location of the material to be removed, the amount of material to be removed, and any other constraints, such as, for example, those discussed above. After identifying the tool for use in each step of the treatment plan, the tool's path, position, and orientation are determined for each of the material removal steps at block 310. In some embodiments, determination of each tool and the determination of the tool's path, position, and orientation are determined together rather than at separate blocks. In some embodiments, the tool position and tool path information may be used to generate instructions for a robotic or a computer controlled material removal process, such as a CNC process.

Figure 3C:
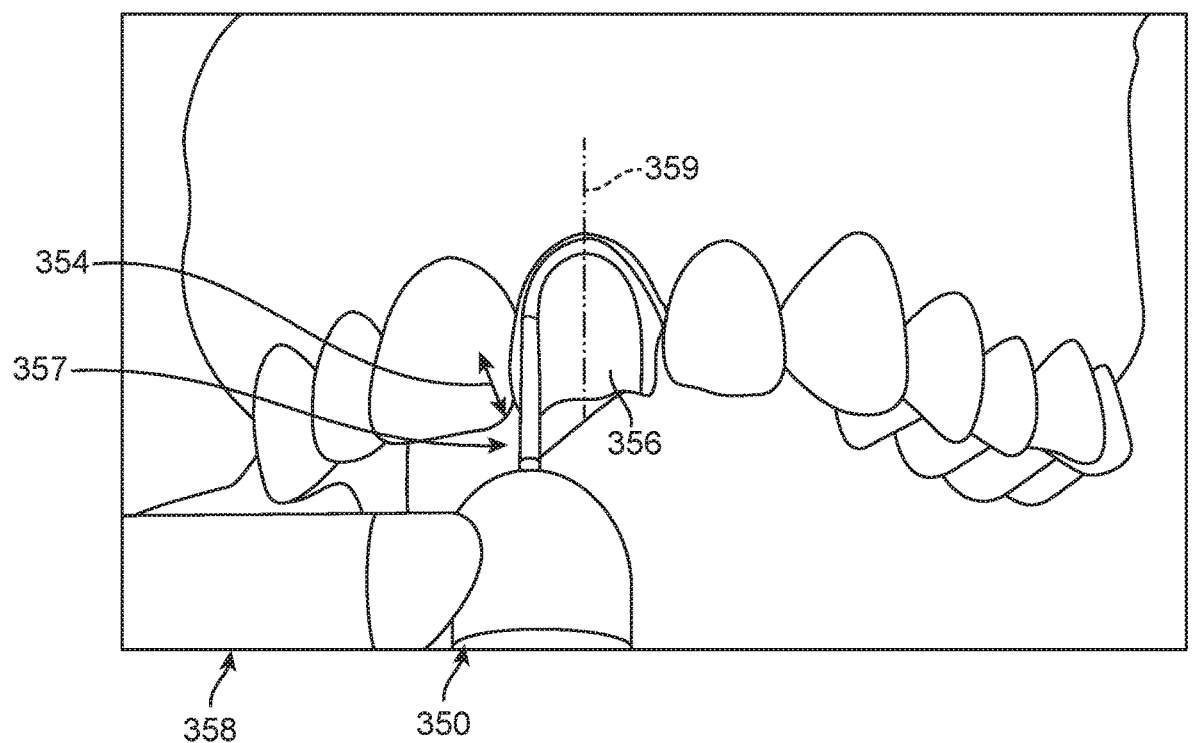
FIGS. 3C and 3D illustrate visualizations of steps of treatment in a treatment plan, in accordance with embodiments.
Figure 3D:
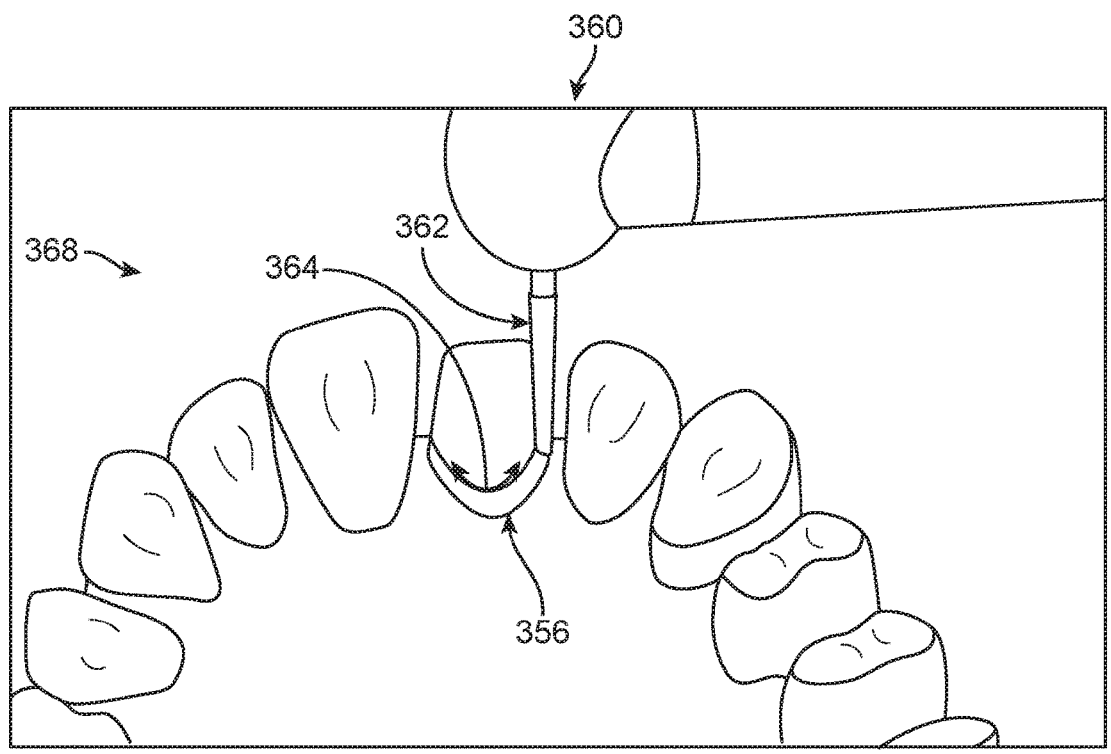

After determination of the tool position and tool path at block 310, the process 300 continues to block 312 where the visualizations for each of the treatment steps are generated. FIGS. 3C and 3D depict visualizations of two steps of the material removal process of a treatment plan. FIG. 3C depicts the proximal preparation of a tooth 356. In FIG. 3C, the buccal surface of the tooth 356 has already been prepared in a previous step of the preparation process. The visualization shows the position and orientation of the tool 350 and the tool head 352 with respect to the tooth 356 being prepared. The orientation of the tool 350 and tool head 352 may be shown with respect to, for example, a central axis 359 of the tooth that extends from the center of the root of the tooth through the center of the occlusal surface of the tooth. The visualization may also include a depiction or indication of the tool type 358 and the tool head type 357. Finally, the visualization also includes an indication of the direction 354 in which the tool head 352 should be moved, including both translation and rotation, in order to remove the appropriate material from the tooth 356 for this particular step of the treatment plan.

Although depicted as a two-dimensional image, the visualization shown in FIG. 3C may be a manipulatable three-dimensional model that allows a practitioner to rotate, zoom, and otherwise manipulate the model such that the practitioner may view the material removal step from several perspectives. Moreover, in some embodiments, the visual depiction may show the procedure in two-dimensional or three-dimensional video or motion forms. In such an embodiment, in addition to indicating the direction of tool movement, the video may depict a simulation of the material removal process including a depiction of the movement of the tool, showing both the directional translation and rotation of the tool's movement and the appropriate speed at which the tool should be moved during the material removal process.

FIG. 3D shows further preparation of the left central upper incisor 356. The visualization shows the position and orientation of the tool 360 and the tool head 362 with respect to the tooth 356 being prepared. The tool 360 and the tool head 362 may be different than the tool 350 and the tool head 352 depicted it in FIG. 3C. As with the treatment step shown in FIG. 3C, the orientation of the tool 360 and tool head 362 may be shown with respect to, for example, a central axis of the tooth 356 that extends from the center of the root of the tooth through the center of the occlusal surface of the tooth. The visualization in FIG. 3D may also include a depiction or indication of the tool type and tool head type. Finally, the visualization may also include an indication of the direction 364 in which the tool head 362 should be moved in order to remove the appropriate material from the tooth 356.

Although depicted as a two-dimensional image, the visualization shown in FIG. 3C may be a manipulatable three-dimensional model that allows a practitioner to rotate, zoom, and otherwise manipulate the model such that the practitioner may view the material removal step from several perspectives. Moreover, in some embodiments, the visual depiction may show the procedure in two-dimensional or three-dimensional video or motion forms. In such an embodiment, in addition to indicating the direction of tool movement, the video may depict a simulation of the material removal process including a depiction of the movement of the tool, showing both the directional translation and rotation of the tool's movement and the appropriate speed at which the tool should be moved during the material removal process.

In some embodiments, at block 312 or block 402, the dental professional may perform simulated material removal in a computer simulated environment with virtual tools, for example tools that resemble actual tools or through the use of digital volume removal tools, that simulate the removal of material, but do not show and simulate the presence of a tool. Such simulated material removal by be shown with a model of a patient's mouth, teeth, and/or gingiva, for example, a volumetric model or a surface model. In such a simulation, as the dental professional moves the virtual tool or the digital volume removal tools model is modified to show the simulated changes to the tooth, for example, the volumetric model may be updated by removing volume from the model or the surface model may be updated to reflect an updated surface profile that reflects the material removed by the dental professional's use of the tool.

One or more of the steps of the method 300 may be performed with circuitry as described herein, for example one or more of a processor or logic circuitry of a computer or a computerized system. The circuitry may be programmed to provide one or more of the steps of the method 300, and the program may comprise program instructions stored on a computer readable memory or programmed steps of the logic circuitry, for example.

Figure 4:
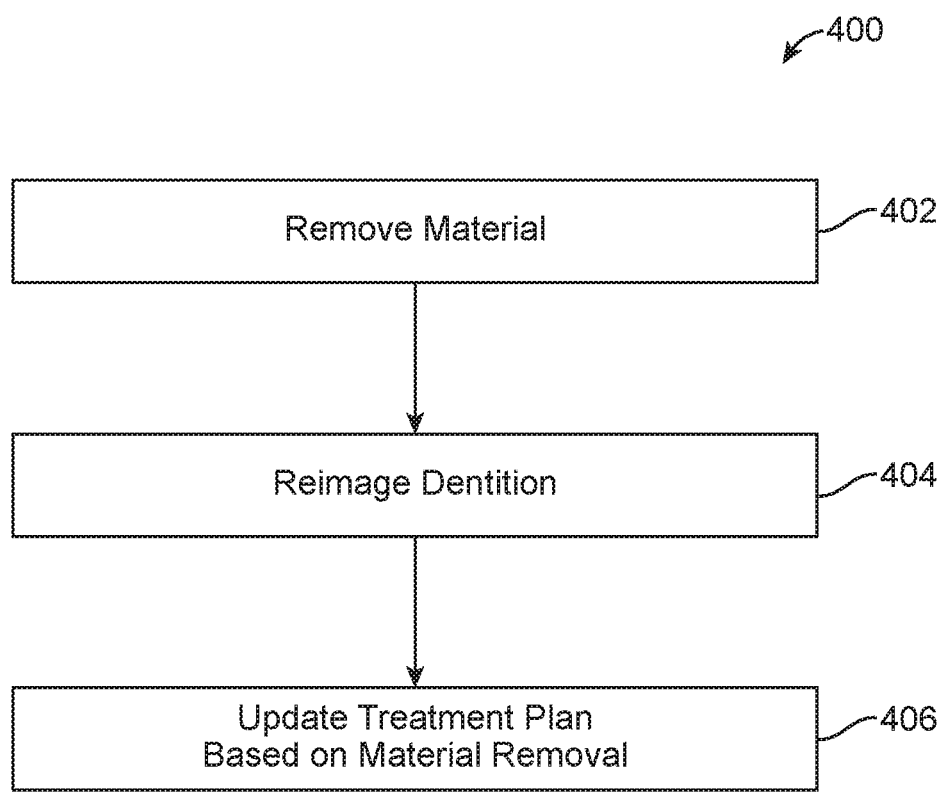
FIG. 4 illustrates a method of evaluating treatment and providing feedback during treatment, in accordance with embodiments.

FIG. 4 illustrates a method 400 of evaluating treatment and providing feedback during treatment, in accordance with embodiments described herein. The method 400 may include material removal, reimaging of the dentition, and updating the treatment plan. At block 402, a dental professional may attempt to remove material from a tooth, as depicted in one or more steps of a treatment plan that was generated in accordance with methods described above. After having removed some material from a patient's tooth, at block 404 the dental professional may rescan the patient's dentition including for example the tooth being prepared. Reimaging of the patient's dentition or tooth may include one or more of the processes discussed above with respect to the imaging conducted at block 202 of method 200, shown and described with respect to FIG. 2A. After reimaging and rebuilding an updated model of the patient's dentition, the model may be marked to indicate the remaining material to be removed from the teeth. For example, updated models, such as the models shown in FIG. 3B, may be generated and shown to potential practitioner. The models may indicate an amount of material to be removed both numerically and also by highlighting the material that remains to be removed on the model (e.g., using a heat map or the like).

In some embodiments, the material may be removed though robotic assisted methods, such as robotic-assisted surgery, wherein a dental professional controls movement of a robot and attached dental tools via a telemanipulator or through computer control. The material removal may also be performed by computer numerical control (CNC) wherein the automation of one or more machine tool is controlled by means of one or more computer executing pre-programmed sequences of machine control commands.

In some embodiments, method 300 for generating visualizations may be repeated based on the updated model. In such an embodiment, updated tool information including tool type, tool position, and tool path may be used to generate updated visualizations of the treatment. In some embodiments the updated visualization made simply depict an updated to a particular step in the treatment plan, such as the current step for removing the remaining tooth material.

However, in some embodiments, a dental practitioner may have removed material that was not indicated for removal according to the treatment plan. In such embodiments, the treatment planning process may be revised using the updated scans. New finalized tooth shapes may be generated according to method 200 shown and described with respect to FIG. 2A and new visualizations may be generated according to method 300 shown and described with respect to FIG. 3A. After generating the updated visualizations, the dental practitioner may continue with treatment. The dentition may be rescanned at block 404 and an updated treatment plan may be generated at block 406 as many times as a dental professional performing the preparation desires and until preparation is complete.

One or more of the steps of the method 400 may be performed with circuitry as described herein, for example one or more of a processor or logic circuitry of a computer or a computerized system. The circuitry may be programmed to provide one or more of the steps of the method 400, and the program may comprise program instructions stored on a computer readable memory or programmed steps of the logic circuitry, for example.

Figure 5:
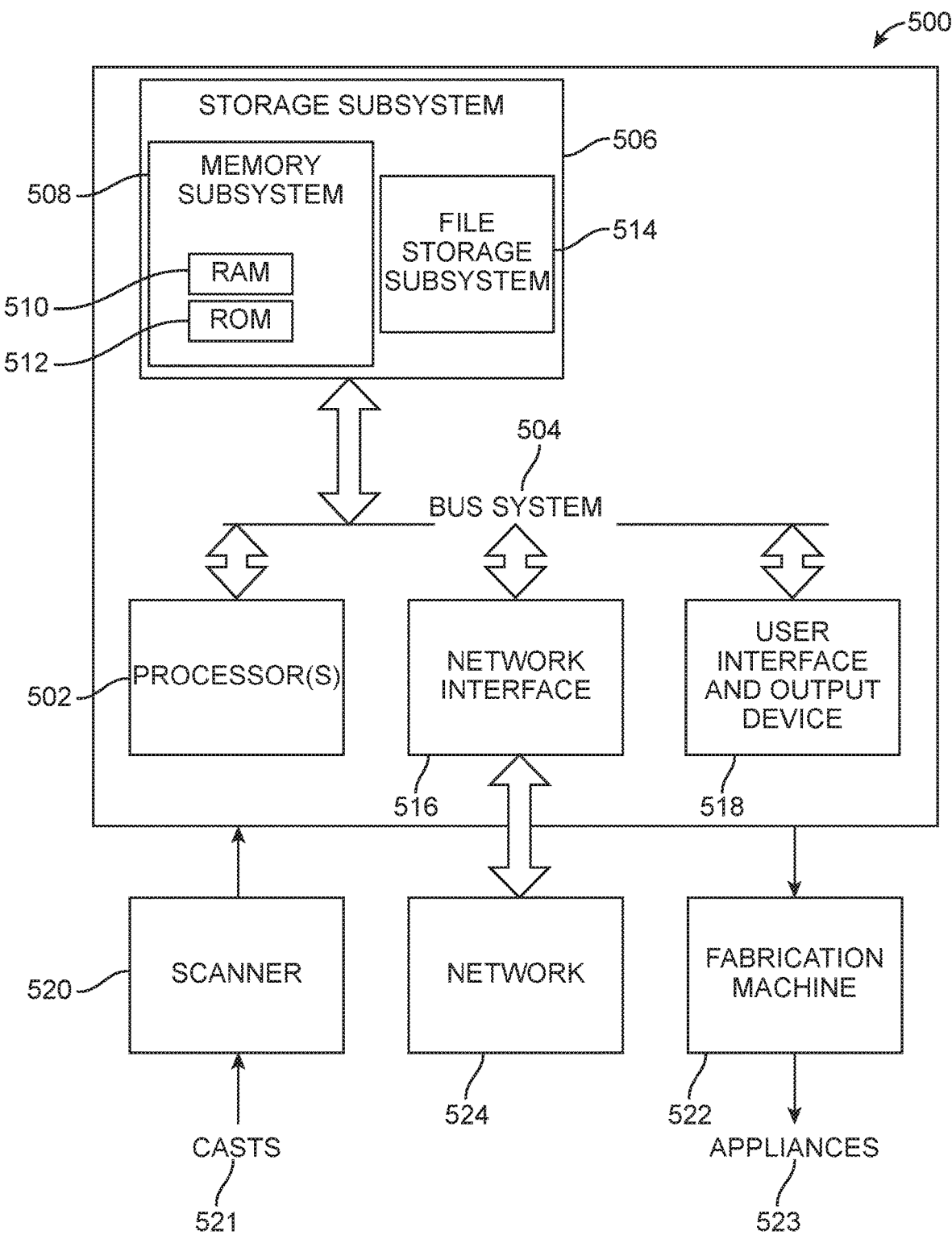
FIG. 5 illustrates a system for carrying out the methods of visual prosthetic and orthodontic treatment planning, in accordance with embodiments.

FIG. 5 illustrates a system for carrying out the methods of visual prosthetic and orthodontic treatment planning, in accordance with embodiments. FIG. 5 is a simplified block diagram of a data processing system 500 that may be used in executing methods and processes described herein. The data processing system 500 typically includes at least one processor 502 that communicates with one or more peripheral devices via bus subsystem 504. These peripheral devices typically include a storage subsystem 506 (memory subsystem 508 and file storage subsystem 514), a set of user interface input and output devices 518, and an interface to outside networks 516. This interface is shown schematically as "Network Interface" block 516, and is coupled to corresponding interface devices in other data processing systems via communication network interface 524. Data processing system 500 can include, for example, one or more computers, such as a personal computer, workstation, mainframe, laptop, and the like.

The user interface input devices 518 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 506 maintains the basic required programming, including computer readable media having instructions (e.g., operating instructions, etc.), and data constructs. The program modules discussed herein are typically stored in storage subsystem 506. Storage subsystem 506 typically includes memory subsystem 508 and file storage subsystem 514. Memory subsystem 508 typically includes a number of memories (e.g., RAM 510, ROM 512, etc.) including computer readable memory for storage of fixed instructions, instructions and data during program execution, basic input/output system, etc. File storage subsystem 514 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 520 includes any means for obtaining a digital representation (e.g., images, surface topography data, etc.) of a patient's teeth (e.g., by scanning physical models of the teeth such as casts 521, by scanning impressions taken of the teeth, or by directly scanning the intraoral cavity), which can be obtained either from the patient or from treating professional, such as an orthodontist, and includes means of providing the digital representation to data processing system 500 for further processing. Scanner 520 may be located at a location remote with respect to other components of the system and can communicate image data and/or information to data processing system 500, for example, via a network interface 524. Fabrication system 522 fabricates appliances 523 based on a treatment plan, including data set information received from data processing system 500. Fabrication machine 522 can, for example, be located at a remote location and receive data set information from data processing system 500 via network interface 524.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A method for preparing a tooth of a patient, the method comprising:
   building a three-dimensional surface model of a dentition of the patient from a three-dimensional surface scan of the patient's dentition;
   building a volumetric model from a scan of an internal structure of the patient's dentition;
   building a three-dimensional composite model comprising a plurality of voxels from the three-dimensional surface model and the volumetric model, thereby building a model of the dentition of the patient including a model of an initial shape of the tooth;
   determining a final prepared shape of the tooth;
   generating a treatment plan comprising a plurality of steps to modify the initial shape of the tooth to the final prepared shape of the tooth; and
   rendering visualizations for the plurality of steps of the treatment plan, the visualizations depicting removal of tooth material to modify the initial shape of the tooth to the final prepared shape of the tooth,
   wherein a voxel of the plurality of voxels comprises a defect type.

2. The method of claim 1, wherein the plurality of voxels each comprise a location within the composite model, a dental structure type of the internal structure, and a density.

3. The method of claim 2, wherein the dental structure type of the internal structure, the density, and the defect type are determined based on an infrared scan of the internal structure of the patient's dentition or an x-ray image of the internal structure of the patient's dentition.

4. The method of claim 1, further comprising:
   determining the material removed for each step of the treatment plan.

5. The method of claim 4, further comprising:
   selecting a tool from a plurality of tools for removing tooth material for each of the plurality of steps; and
   selecting a tool head from a plurality of tool heads for removing tooth material for each of the plurality of steps.

6. The method of claim 5, further comprising:
   determining a movement path for each selected tool for removing material for the plurality of steps in the treatment plan.

7. The method of claim 6, wherein the movement path includes an indication of a direction of translation and an orientation of the tool head.

8. The method of claim 1, wherein the visualizations are three-dimensional visualizations.

9. The method of claim 1, wherein the visualizations are three-dimensional, video simulation of the material removal for the plurality of steps of the treatment plan.

10. The method of claim 1, further comprising:
    receiving constraints on the final prepared shape of the tooth; and
    generating a plurality of suggested final prepared shapes of the tooth based on the constraints.

11. The method of claim 10, further comprising:
    receiving a selection of the final prepared shape from the plurality of suggested final prepared shapes, and wherein determining the final prepared shape of the tooth is based on the received selection of the final prepared shape.

12. A method for preparing a tooth of a patient, the method comprising:
building a model of a dentition of the patient including a model of an initial shape of the tooth;
determining a final prepared shape of the tooth;
generating a treatment plan comprising a plurality of steps to modify the initial shape of the tooth to the final prepared shape of the tooth;
rendering visualizations for the plurality of steps of the treatment plan, the visualizations depicting removal of tooth material to modify the initial shape of the tooth to the final prepared shape of the tooth;
reimaging the patient's dentition after removing a portion of material according to a step of the treatment plan to build an updated dentition model including an updated model shape of the patient's tooth;
comparing the updated dentition model with a dentition model for the step of the treatment plan; and
highlighting remaining material that should be removed according to the step of the treatment plan.

13. The method of claim 12, further comprising:
determining an updated final prepared shape of the tooth;
generating an updated treatment plan comprising a second plurality of steps to modify the updated model shape of the tooth to the updated final prepared shape of the tooth; and
rendering second visualizations for the second plurality of steps of the updated treatment plan, the second visualizations depicting removal of tooth material to modify the updated model shape of the tooth to the updated final prepared shape of the tooth.

14. The method of claim 13, wherein the final prepared shape of the tooth is the same as the updated final prepared shape of the tooth.

15. A system for aiding in preparing a tooth of a patient, the system comprising:
one or more processors and memory, wherein the memory comprises instructions executable by the one or more processors to cause the system to:
build a three-dimensional surface model of a dentition of the patient from a three-dimensional surface scan of the patient's dentition;
combine the three-dimensional surface model of the patient's dentition with an imagery of the internal structure of the patient's dentition to form a three-dimensional, composite model of the patient's dentition comprising a plurality of voxels, thereby building a model of a dentition of the patient including a model of an initial shape of the tooth;
generate a treatment plan comprising a plurality of steps to modify the initial shape of the tooth to a final prepared shape of the tooth; and
render visualizations for the plurality of steps of the treatment plan, the visualizations depicting removal of tooth material to modify the initial shape of the tooth to the final prepared shape of the tooth,
wherein a voxel of the plurality of voxels comprises a defect type.

16. The system of claim 15, wherein the plurality of voxels each comprise a location within the volumetric model, a dental structure type of the internal structure, and a density.

17. The system of claim 16, wherein the dental structure type of the internal structure, the density, and the defect type are determined based on an infrared scan of the internal structure of the patient's dentition or an x-ray image of the internal structure of the patient's dentition.

18. The system of claim 15, wherein the memory further comprising instructions executable by the one or more processors to cause the system to:
determine the material removed for each step of the treatment plan.

19. The system of claim 18, wherein the memory further comprises instructions executable by the one or more processors to cause the system to:
select a tool from a plurality of tools for removing tooth material for each of the plurality of steps; and
select a tool head from a plurality of tool heads for removing tooth material for each of the plurality of steps.

20. The system of claim 15, wherein the memory further comprises instructions executable by the one or more processors to cause the system to:
determine a movement path for each selected tool for removing material for the plurality of steps in the treatment plan.

21. The system of claim 20, wherein the movement path includes an indication of a direction of translation and an orientation of the tool head.

22. The system of claim 15, wherein the visualizations are three-dimensional visualization.

23. The system of claim 15, wherein the visualizations are a three-dimensional, video simulation of the material removal for the plurality of steps of the treatment plan.

24. The system of claim 15, wherein the memory further comprises instructions executable by the one or more processors to cause the system to:
receive constraints on the final prepared shape of the tooth; and
generate a plurality of suggested final prepared shapes of the tooth based on the constraints.

25. The system of claim 24, wherein the memory further comprises instructions executable by the one or more processors to cause the system to:
receive a selection of the final prepared shape from the plurality of suggested final prepared shapes, and wherein determining the final prepared shape of the tooth is based on the received selection of the final prepared shape.

26. A system for aiding in preparing a tooth of a patient, the system comprising:
one or more processors and memory, wherein the memory comprises instructions executable by the one or more processors to cause the system to:
build a model of a dentition of the patient including a model of an initial shape of the tooth;
generate a treatment plan comprising a plurality of steps to modify the initial shape of the tooth to a final prepared shape of the tooth;
render visualizations for the plurality of steps of the treatment plan, the visualizations depicting removal of tooth material to modify the initial shape of the tooth to the final prepared shape of the tooth;
receive an updated image of the patient's dentition after removing a portion of material according to a step of the treatment plan to build an updated dentition model including an updated model shape of the patient's tooth;
compare the updated dentition model with a dentition model for the step of the treatment plan; and highlight remaining material that should be removed according to the step of the treatment plan.

27. The system of claim 26, wherein the memory further comprises instructions executable by the one or more processors to cause the system to:
determine an updated final prepared shape of the tooth;
generate an updated treatment plan comprising a second plurality of steps to modify the updated model shape of the tooth to the updated final prepared shape of the tooth; and
render second visualizations for the second plurality of steps of the updated treatment plan, the second visualizations depicting removal of tooth material to modify the updated model shape of the tooth to the updated final prepared shape of the tooth.

28. The system of claim 27, wherein the final prepared shape of the tooth is the same as the updated final prepared shape of the tooth.

* * * * *